United States Patent [19]

Hara et al.

[11] Patent Number: 4,816,686
[45] Date of Patent: * Mar. 28, 1989

[54] METHOD AND APPARATUS FOR DETECTING WIRING PATTERNS

[75] Inventors: Yasuhiko Hara, Yokohama; Koichi Karasaki; Noriaki Ujiie, both of Hadano, all of Japan

[73] Assignee: Hitachi, Ltd., Tokyo, Japan

[*] Notice: The portion of the term of this patent subsequent to Jun. 9, 2004 has been disclaimed.

[21] Appl. No.: 832,692

[22] Filed: Feb. 25, 1986

Related U.S. Application Data

[63] Continuation of Ser. No. 619,918, filed Jun. 12, 1984 abandoned.

[30] Foreign Application Priority Data

Jun. 16, 1983 [JP] Japan ................................ 58-106750
Jun. 21, 1983 [JP] Japan ................................ 58-111414

[51] Int. Cl.4 ...................... G01N 21/88; G01N 21/64
[52] U.S. Cl. ................................ 250/458.1; 250/459.1; 356/237; 358/106

[58] Field of Search ..................... 356/237; 250/458.1, 250/461.1, 302, 459.1; 358/106

[56] References Cited

U.S. PATENT DOCUMENTS

| | | | |
|---|---|---|---|
| 3,617,744 | 11/1971 | Irish | 250/461.1 |
| 4,087,685 | 5/1978 | Froot | 250/302 |
| 4,152,723 | 5/1979 | McMahon et al. | 250/458.1 |
| 4,284,897 | 8/1981 | Sawamura et al. | 250/461.2 |
| 4,364,088 | 12/1982 | Kubota | 356/23 |
| 4,421,410 | 12/1983 | Karasaki | 356/237 |
| 4,536,654 | 8/1985 | Vaerman | 250/302 |
| 4,608,494 | 8/1986 | Kobayashi et al. | 250/458.1 |
| 4,672,209 | 6/1987 | Karasaka et al. | 250/461.1 |
| 4,679,938 | 7/1987 | Flamholz | 250/458.1 |
| 4,700,225 | 10/1987 | Hara et al. | 358/106 |

Primary Examiner—Carolyn E. Fields
Attorney, Agent, or Firm—Antonelli, Terry & Wands

[57] ABSTRACT

Method and apparatus for detecting wiring patterns wherein a printed circuit board is irradiated with a light ray which excites a substrate of the printed circuit board to generate a fluorescent radiation from the substrate, the fluorescent radiation generated from portions other than a wiring pattern of the printed circuit board is imaged by means of an image detector, and a negative pattern of the wiring pattern is detected on the basis of an image signal generated from the image detector.

36 Claims, 13 Drawing Sheets

METHOD AND APPARATUS FOR DETECTING WIRING PATTERNS

This is a continuation of application Ser. No. 619,918, filed June 12, 1984, now abandoned.

BACKGROUND OF THE INVENTION

The present invention relates to detection of the presence or absence of defects of wiring patterns and more particularly, to method and apparatus suitable for detecting wiring patterns such as glossy soldering patterns or resist patterns on a printed circuit board.

In the past, for detection of the presence or absence of defects of wiring patterns formed on the surface of, for example, a printed circuit board, a detecting apparatus as shown in FIG. 1 has been used typically.

This example of the wiring pattern detecting apparatus comprises a light source 11 of high luminance for irradiating light 31 on a wiring surface 2 (surface on which a wiring pattern is formed) of a substrate 4 (see FIG. 2) such as a polyimide substrate or a epoxy substrate of a printed circuit board 1, a condensor lens 21, a half-mirror 23, a detector 13 for detecting reflected light 45 from the wiring surface 2, and a focusing lens 25 for focusing a wiring pattern image on the detector 13. Due to the fact that the reflected light from the surface of the substrate 4 is more proximate to a dark level than the reflected light 45 from the wiring pattern 3 on the wiring surface 2 of the substrate 4, the wiring pattern image is resolved into binary levels and its positive pattern signal is detected.

FIG. 2 shows one example of the printed circuit board that is an object to be detected. As shown, a wiring pattern 3 is formed on a wiring surface 2 of a substrate 4.

In a printed circuit board 1 exemplified in FIG. 2, a flaw 5 and a discolored portion 7 appear on the wiring pattern 3, and a copper residue 6 bridges across adjacent pattern conductors.

The flaw 5 is sectioned on line IIIA—IIIA in FIG. 2 so as to be depicted in FIG. 3A, the copper residue 6 is sectioned on line IIIB—IIIB so as to be depicted in FIG. 3B, and the discolored portion 7 is sectioned on line IIIC—IIIC so as to be depicted in FIG. 3C.

When the printed circuit board 1 having the defects shown in FIG. 2 is inspected with the conventional wiring pattern detecting apparatus shown in FIG. 1, the flaw portion 5 and the discolored portion 7 are erroneously detected as disconnections in spite of the fact that pattern conductors really underlie these portions and are satisfactory to function normally. In addition, the copper residue 6 is, in effect, a defect which short circuits across the adjacent pattern conductors but its surface is seen dark, resulting in failure to detect the defect.

Referring to FIGS. 4a to 4c, the erroneously detected states in the conventional apparatus (FIG. 1) as described thus far will now be explained. In these figures, the abscissa represents the position and the ordinate represents the voltage resulting from the photoelectric conversion by the detector 13. In particular, voltage $V_0$ denotes a dark level occurring at a through-hole 8, voltage $V_2$ a level occurring at the wiring pattern 3, voltage $V_3$ a saturation level of the detector 13, and voltage $V_T$ a threshold level. As shown in FIG. 4a, when abnormally intensive positive reflection light from the flaw 5 comes into the detector 13 at a position A', this detector 13 reaches the saturation voltage $V_3$ to cause a blooming phenomenon wherein the voltage goes beyond and below the threshold level $V_T$ alternately and an abnormal state is detected at the position A'. At a position C' corresponding to the discolored portion 7, because of a low reflection factor of the discolored portion 7, voltage $V_5$, which cannot reach the voltage $V_2$ corresponding to the normal wiring pattern 3, falling below the threshold level $V_T$, may be obtained at the most as shown in FIG. 4c, and hence the absence of the wiring pattern 3, that is, a disconnection is erroneously detected at the position C'. Further, at a position B' corresponding to the copper residue 6, voltage $V_4$ which cannot reach the voltage $V_2$ corresponding to the normal wiring pattern 3, falling below the threshold level $V_T$, may be obtained at the most as shown in FIG. 4b, and hence the detection at the position B' is such that the presence of the copper residue 6 is disregarded.

In addition, at a surface portion of the wiring pattern 3 consisting of a so-called soldering pattern formed by plating glossy solder, because of its gloss, abnormally intensive positive reflection light, glittering at the soldering pattern, comes into the detector 13, resulting in a similar phenomenon to that resulting from the presence of the flaw 5 on the wiring pattern 3, and hence an abnormality is erroneously detected despite the normality of the printed circuit board 1. For these reasons, the conventional pattern detection apparatus fails to ensure correct detection of the patterns.

SUMMARY OF THE INVENTION

The present invention contemplates the elimination of the drawbacks of the conventional apparatus and has for its object to provide a method and apparatus for detecting wiring patterns which can prevent such an erroneous detection that the flaw and discoloration on a wiring pattern made of a metallic material are detected as defects, which can detect a copper residue responsible for making a printed circuit board defective, without disregarding the copper residue, and which can correctly detect the presence or absence of defects on a wiring pattern having a glossy surface, such as a soldering pattern surface, or a resist pattern surface.

The inventors of the present application have been engaged in studying the method of obtaining an image of a wiring pattern, by which method not only the influence of the flaw, discoloration and glossy defects can be eliminated but also the detection of the copper residue having the small surface reflection factor can be ensured, and have formed that when intensive light of violet series rays is irradiated on the printed circuit board and resist pattern as well as on the wiring surface of the ceramic substrate, the substrate and the resist are excited to emit fluorescent radiations and negative image of a wiring pattern, standing for an object to be detected, can be obtained by detecting the fluorescent radiations.

For correct detection of the presence or absence of defects of wiring patterns based on the above principle, a pattern detecting apparatus according to this invention comprises a source of light for emitting light rays to be irradiated on a wiring pattern formed on a wiring surface of an object to be detected, means for selecting among the light rays emitted from the light source a light ray of a wavelength having great ability to generate a fluorescent radiation from the object, means for separating the fluorescent radiation generated from the object from reflected light rays from the object, a detector for detecting the fluorescent radiation, and optical means for focusing the fluorescent radiation generated from the object on the detector, whereby an image of the fluorescent radiation generated from portions on the wiring surface of the object excepting the wiring pattern is detected to obtain a negative pattern of the wiring pattern.

Specifically, intensive light of violet series rays may be irradiated on front and rear sides of the object to be detected to generate an intensive fluorescent radiation from the substrate and resist, and the intensive fluorescent radiation may be detected to obtain a negative image of the wiring pattern at a high signal to noise ratio. Preferably, the intensive violet series light is obliquely irradiated on the rear side of the object to prevent the wiring pattern on the rear side from shadowing the incident light.

DESCRIPTION OF THE PREFERRED EMBODIMENTS

Figure 5:
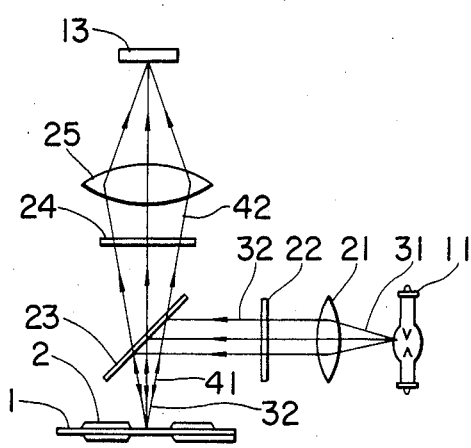
FIG. 5 is side schematic of a wiring pattern detecting apparatus according to one embodiment of the invention.
Figure 6:
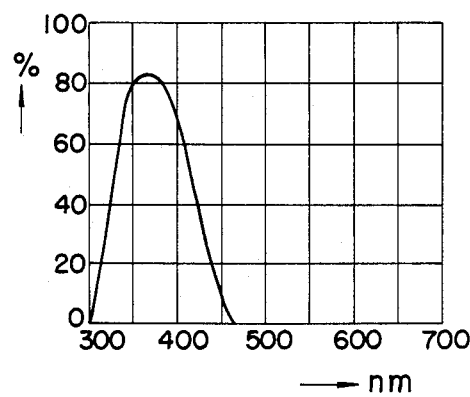
FIGS. 6 and 7 are graphs showing characteristics of filters used in the embodiment of FIG. 5.
Figure 7:
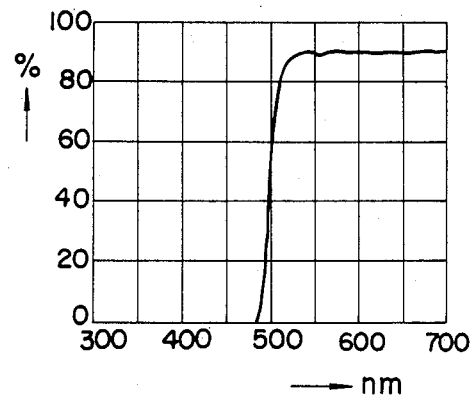

Referring now to FIGS. 5 to 7, a wiring pattern detecting apparatus according to a preferred embodiment of the present invention will now be described.

Figure 1:
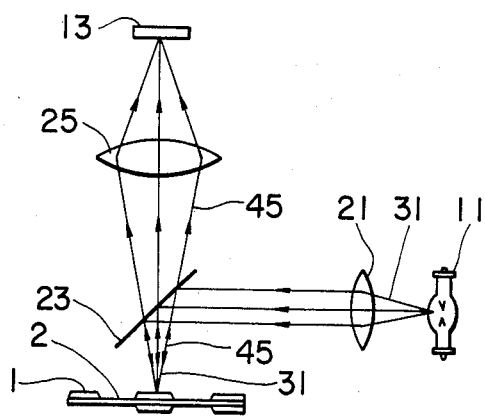
FIG. 1 is a side schematic of a prior art wiring pattern detecting apparatus.

In the pattern detecting apparatus of this invention as schematically shown in FIG. 5, a printed circuit board 1, a light source 11 of high luminance, a condensor lens 21, a half-mirror 23, a focusing lens 25 and a detector 13 correspond to those of the prior art pattern detecting apparatus shown in FIG. 1 and are arranged in the same manner, but filters 22 and 24 are newly added. In FIG. 5, light rays 31 emitted from the light source 11 of high luminance pass through the condensor lens 21 and come into the filter 22. This filter 22 is adapted to select among the light rays 31 emitted from the light source 11 a light ray of a wavelength which can facilitate generation of a fluorescent radiation from the printed circuit board substrate, a resist pattern and a ceramic substrate. For example, the filter 22 is a so-called blue filter which transmits only a light ray of a wavelength ranging from 300 to 460 nm with a maximum transmittivity at 370 nm as shown in FIG. 6. The light ray of the selected wavelength, designated at 32, is incident to the half-mirror 23 and is changed thereby in its path through 90° so as to be irradiated on a wiring surface 2 of the printed circuit board 1, thus acting as an exciting light ray for generating a fluorescent radiation from the substrate or resist. The fluorescent radiation generated from the substrate or resist is mixed with a reflected light ray from the wiring surface 2 to produce light rays 41 which come into the filter 24 after passing through the half-mirror 23. The filter 24 is adapted to separate the fluorescent radiation from the reflected light ray from the wiring surface 2 of the printed circuit board 1 and transmits only the fluorescent radiation designated at 42 having a wavelength different from that of the exciting light ray 32. For example, the filter 24 is a so-called yellow filter which reflects a light ray of a wavelength of less than 500 nm and transmits a light ray of a wavelength of more than 500 nm as shown in FIG. 7. The fluorescent radiation 42, separated from the reflected light ray from the wiring surface 2 by means of the filter 24, is focused by the focusing lens 25 on a photoelectric conversion surface of the detector 13, thereby producing a negative image of a wiring pattern on the printed circuit board 1.

Figure 2:
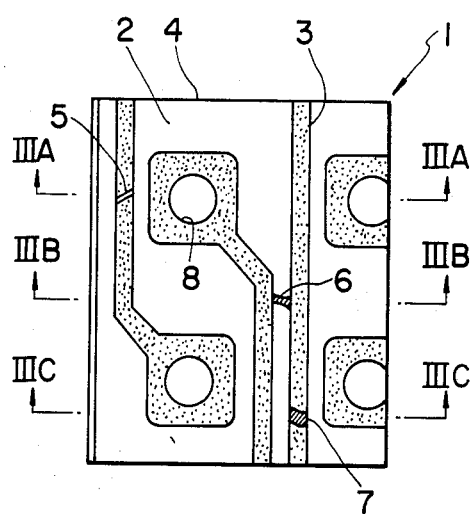
FIG. 2 is a plan view of a printed circuit board.
Figure 3A:
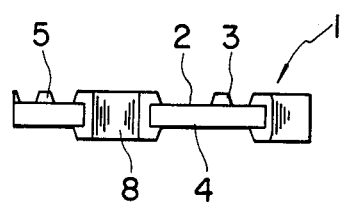
FIG. 3A is a sectional view taken on line IIIA—IIIA of FIG. 2.
Figure 3B:
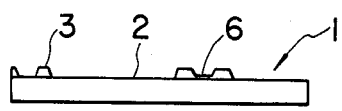
FIG. 3B is a sectional view taken on line IIIB—IIIB of FIG. 2.
Figure 3C:
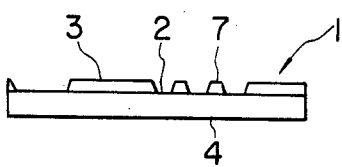
FIG. 3C is a sectional view taken on line IIIC—IIIC of FIG. 2.
Figure 4A:
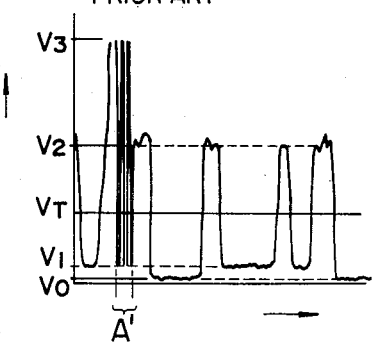
FIG. 4A to 4C are graphical representations showing detection results obtained with the prior art wiring pattern detecting apparatus.
Figure 4B:
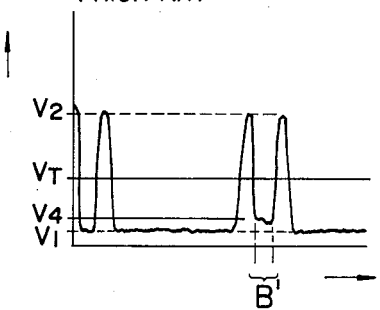
Figure 4C:
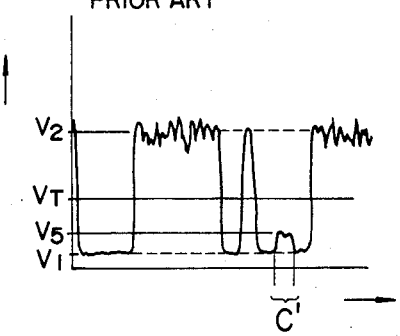
Figure 8A:
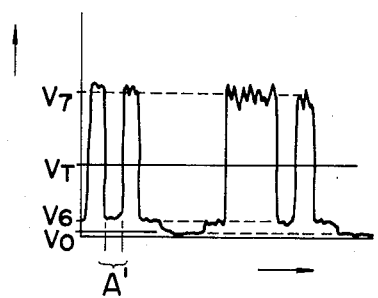
FIGS. 8A to 8C are graphical representations showing detection results obtained with the apparatus of the FIG. 5 embodiment.
Figure 8B:
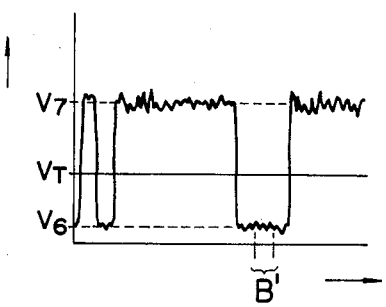
Figure 8C:
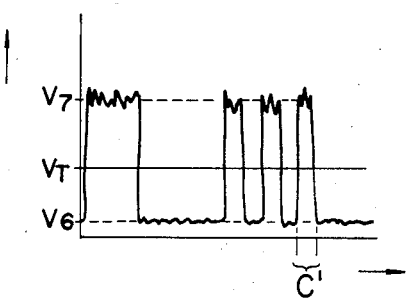

As described above, since the pattern detecting apparatus according to the FIG. 5 embodiment of this invention acts to detect a fluorescent radiation generated from the resist pattern and ceramic substrate, this apparatus can detect a negative image of a wiring pattern without being affected by the flaw 5 and discolored portion 7 present on the wiring pattern 3 as shown in FIG. 2 as well as by gloss of the wiring pattern. In addition, in the event that the copper residue 6 having a small reflection factor exists on the surface of the substrate 4 as shown in FIG. 2, a fluorescent radiation generated from a portion of the substrate 4 underlying the copper residue 6 will be interrupted thereby so as not to be detected and the presence of a defect will be indicated. These states will now be described with reference to FIGS. 8A to 8C showing detection results. As in FIGS. 4A to 4C, abscissa represents the position and ordinate represents the voltage resulting from the photoelectric conversion by the detector 13 in FIGS. 8A to 8C. In particular, volta $V_0$ denotes a dark level occurring at a through-hole 8, voltage $V_6$ a level occurring at the wiring pattern 3, voltage $V_7$ a level of the substrate 4, and voltage $V_T$ a threshold level. FIGS. 8A to 8C show, like FIGS. 4A to 4C, voltage levels detected by the detector 13 respectively at the flaw 5, copper residue 6 and discolored portion 7 shown in FIGS. 2 and 3A to 3C. At a position A' corresponding to the flaw 5, because of the fact that the fluorescent radiation is not detected, the level of voltage $V_6$, which is below the threshold level $V_T$, may be obtained as shown in FIG. 8A and the flaw 5 may be detected as the normal wiring pattern. At a position C' corresponding to the discolored portion 7, because of the absence of the detected fluorescent radiation, the level of voltage $V_6$, which is below the threshold level $V_T$, may also be obtained as shown in FIG. 8C and the discolored portion 7 may be detected as the normal wiring pattern. At a position B' corresponding to the copper residue 6, because of the absence of the detected fluorescent radiation, the level of voltage $V_6$, which is below the threshold level $V_T$, may be obtained as shown in FIG. 8B, and the copper residue 6 may be detected as a defect and the presence of the copper residue 6 may be recognized.

In addition, the wiring pattern 3 can be detected correctly at the so-called soldering pattern where the surface of the wiring pattern is formed by plating glossy solder, by detecting the fluorescent radiation from the substrate 4 shown in FIG. 2 as has been described in the precedence.

Preferably, a superhigh pressure mercury-arc lamp, a xenon lamp or a laser may be used as the high luminance light source 11 in the FIG. 5 embodiment since this type of light source emits light rays containing a wavelength having great ability to generate the fluorescent radiation. In this embodiment of FIG. 5, a high sensitivity linear array sensor may preferably be used as the detector 13 to obtain a still picture. In this case, in order to detect a still negative picture of the wiring pattern, the printed circuit board 1 is continuously fed in a direction vertical to the array of photoelectric elements of the high sensitivity linear array sensor and at the same time, fed stepwise in a direction parallel to the array.

Figure 9:
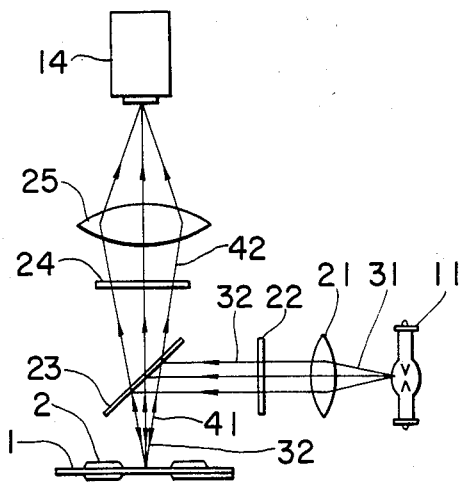
FIGS. 9 and 10 are side schematics showing pattern detecting apparatus according to modified embodiments, starting from the FIG. 5 embodiment, of the invention.

FIG. 9 shows a modification of the FIG. 5 embodiment. In FIG. 9, a printed circuit board 1, a light source 11 of high luminance, a condensor lens 21, a filter 22, a half-mirror 23, a filter 24 and a focusing lens 25 correspond to those of the FIG. 5 embodiment and arranged in the same manner. Being different from the FIG. 5 embodiment, this modification employs a high sensitivity television camera 14 as the detector and operates in the same manner as the FIG. 5 embodiment excepting that the printed circuit board 1 is scanned. The printed circuit board 1 is fed stepwise in row and column directions to obtain wiring pattern information two-dimensionally, and thus, a negative image of the wiring pattern 3 can be detected.

Figure 10:
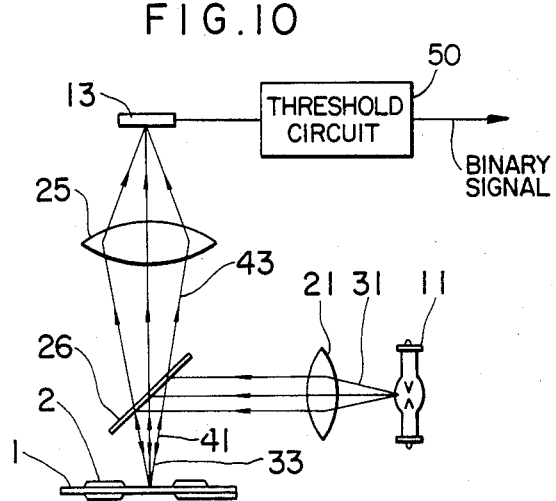
Figure 11:
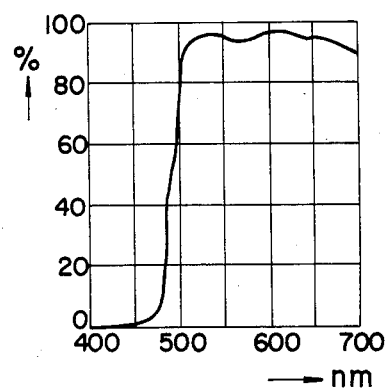
FIG. 11 is a graph showing a characteristic of a dichroic mirror used in the FIG. 10 modification.

FIG. 10 shows a further modification. In FIG. 10, a printed circuit board 1, a high luminance light source 11, a condensor lens 21, a focusing lens 25 and a linear array sensor 13 correspond to those of the FIG. 5 embodiment and are arranged in the same manner. What is different from the FIG. 5 embodiment is that the filter 22, half-mirror 23 and filter 24 are replaced by a dichroic mirror 26. Accordingly, in comparison with the conventional wiring pattern detecting apparatus shown in FIG. 1, the principal difference resides in that the half-mirror 23 of FIG. 1 is replaced with the dichroic mirror 26. In FIG. 10, light rays 31 emitted from the high luminance light source 11 pass through the condensor lens 21 and come into the dichroic mirror 26. This dichroic mirror 26 is characteristic in that for light rays obliquely incident to the dichroic mirror at an angle of 45°, it reflects a blue series light ray and transmits a red series light ray. For example, upon reception of the obliquely incident light rays at 45°, the dichroic mirror has a transmittivity of 0 (zero) % for a light ray of a wavelength of less than 460 nm and a transmittivity of 90% or more for a light ray of a wavelength of more than 510 nm as shown in FIG. 11. Accordingly, the dichroic mirror 26 selects among the light rays 31 obliquely incident thereto at 45° a light ray of less than 460 nm wavelength, which is changed, in its path through 90° so as to be perpendicularly irradiated on the wiring surface 2 of the printed circuit board 1. In this manner, the dichroic mirror 26 performs a hybrid function to act as the filter 22 and half-mirror 23 of the FIG. 5 embodiment in combination, and the irradiating light ray acts as an exciting light ray for generating a fluorescent radiation from the substrate or resist. The fluorescent radiation generated from the substrate or resist is mixed with a reflected light ray from the wiring surface 2 to produce light rays 41 which come into the dichroic mirror 26. At this time, the dichroic mirror 26 permits a red series light ray to be transmitted therethrough and a thus transmitted light ray 43, removed of the reflected light ray from the wiring surface 2 of the printed circuit board 1, contains only the fluorescent radiation. In this manner, the dichroic mirror 26 fulfils the hybrid fuction also meeting the function of the filter 24 in the FIG. 5 embodiment. The fluorescent radiation 43 is focused on the photoelectric conversion surface of the linear array sensor 13 by means of the focusing lens 25, thereby producing a negative image of the wiring pattern on the printed circuit board 1 as in the embodiment of FIG. 5 upon detection by a threshold circuit 50 and converting the detected image signal to a binary signal. Since the dichroic mirror 26 can greatly mitigate reduction of light transmittivity as compared to the embodiment using the filter 22, half-mirror 23 and filter 24, a pattern detecting apparatus suitable for detection of a small quantity of fluorescent radiation can be obtained in accordance with the FIG. 10 embodiment.

Figure 12:
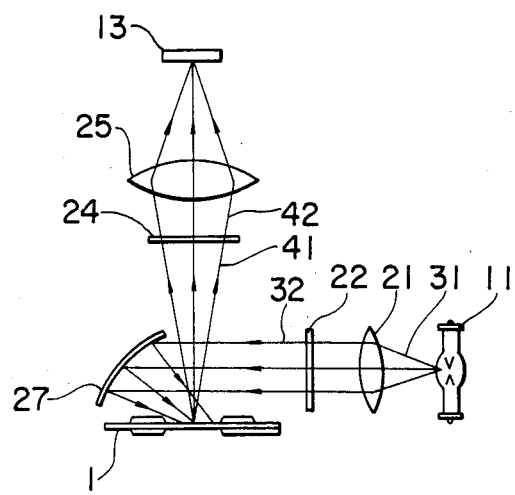
FIGS. 12 to 15 are side schematics showing further modified embodiments.

FIG. 12 shows a further modified embodiment wherein a printed circuit board 1, a high luminance light source 11, a condensor lens 21, filter 22 and 24, a focusing lens 25 and a linear array sensor 13 are identical to those of the FIG. 5 embodiment but a concave mirror 27 substitutes for the half-mirror 23. In place of the concave mirror 27, a plane mirror (not shown) may be used. The operation of this embodiment is the same as that of the FIG. 5 embodiment and will not described herein. Since the concave mirror (or plane mirror) 27 can reduce the loss of light quantity as compared to that due to reflection and transmission at the half-mirror 23 of FIG. 5, this embodiment advantageously permits the provision of a pattern detecting apparatus suitable for detection of small quantity of fluorescent radiation.

Figure 13:
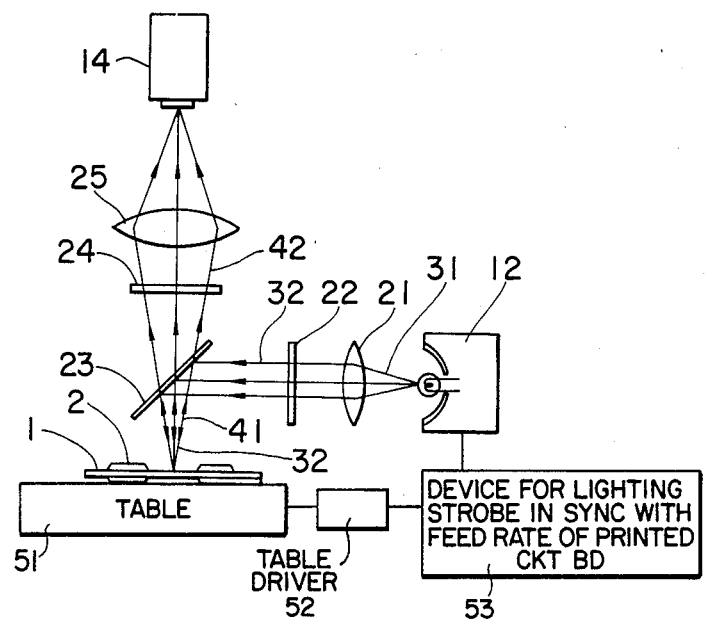

FIG. 13 shows a further modified embodiment wherein a printed circuit board 1, a condensor lens 21, a filter 22, a half-mirror 23, a filter 24, a focusing lens 25 and a high sensitivity television camera 14 are identical to those of the FIG. 9 modification but a stroboscope 12 substitutes for the high luminance light source 11. Except for scanning of the printed circuit board 1, the operation of this embodiment is the same as that of the FIG. 9 modification.

The printed circuit board 1 which is mounted on a table 51 is continuously fed in either one of longitudinal and lateral directions by a table drivers 52 and the stroboscope 12 is lit up in synchronism with a feed rate of the printed circuit board 1 by a device 53, so that two-dimensional information of the wiring pattern can be detected as still image to provide a negative image of the wiring pattern 3. This embodiment can detect the still image during the continuous feed of the printed circuit board 1, without requiring that the printed circuit board 1 be fed stepwise as in the embodiment using the high luminance light source 11 and advantageously, can greatly reduce the time for detection of the wiring pattern.

Figure 14:
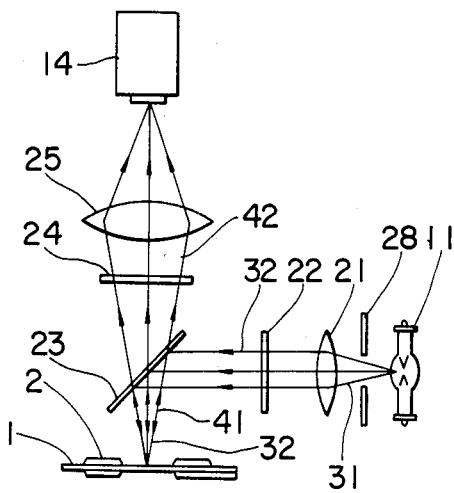

FIG. 14 shows a still further modification wherein a printed circuit board 1, a high luminance light source 11, a condensor lens 21, a filter 22, a half-mirror 23, a filter 24, a focusing lens 25 and a high sensitivity television camera 14 are identical to those of the FIG. 9 modification but a shutter 28 is newly added. Except for scanning of the printed circuit board 1, the operation of this embodiment is the same as that of the FIG. 9 embodiment and will not be described herein. In FIG. 14, an operation comparable to the timed lightup of the stroboscope 12 in FIG. 13 is performed by opening or closing the shutter, and the detection of a still negative image of the wiring pattern 3 is carried out in the same manner as the FIG. 13 modification and will not be described herein.

Figure 15:
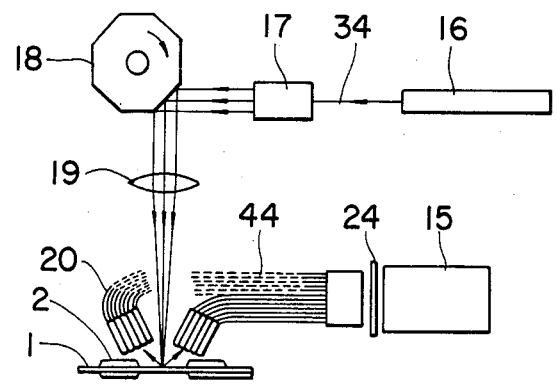

FIG. 15 shows a still further modified embodiment, which comprises a laser 16 for emitting a light beam 34 to be irradiated on a wiring surface 2 on a ceramic substrate of a printed circuit board 1, a beam expander 17 for expanding the laser light beam, a rotary mirror 18 for scanning the laser beam on the wiring surface 2, a scanning lens 19 for focusing the laser beam to a spot beam, a set of optical fibers 20 for efficiently collecting a fluorescent radiation generated from a resist pattern or the ceramic substrate 4 and guiding the collected fluorescent radiation to a detector, a filter 24 for cutting off a reflected light ray from the wiring surface 2 and transmitting only the fluorescent radiation, and a photomultiplier 15 serving as the detector for detection of the fluorescent radiation. The laser beam 34 emitted from the laser 16 and having a wavelength specified to facilitate the generation of the fluorescent radiation is expanded by the beam expander 17, and scanned by the rotary mirror 18 so that a spot beam formed by the scanning lens 19 is irradiated on the wiring surface 2 for scanning predetermined positions of the wiring surface 2. When the spot beam is irradiated on the substrate 4 or resist, a fluorescent radiation is generated, but with the spot beam irradiated on the wiring pattern 3, no fluorescent radiation is generated. The generated fluorescent radiation is collected into the optical fibers 20 and after being passed through the filter 24 which has a light transmittivity of 0 (zero) % for the wavelength range of the laser beam to permit only the fluorescent radiation to transmit therethrough, the fluorescent radiation is detected by the photomultiplier 15. Accordingly, this embodiment, like the previous embodiments, ensures the production of a negative image of a wiring pattern of the printed circuit board.

Figure 16:
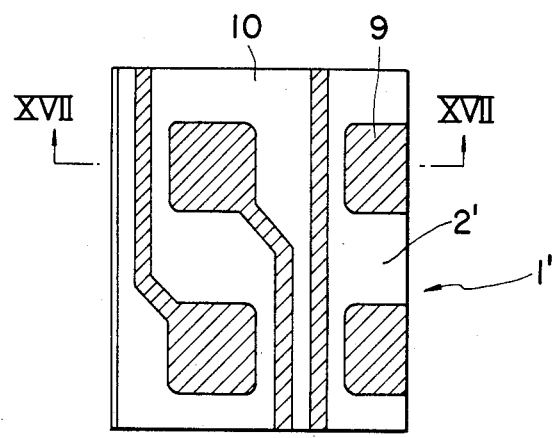
FIG. 16 is a plan view of a semifinished product of a printed circuit board with a resist wiring pattern.
Figure 17:
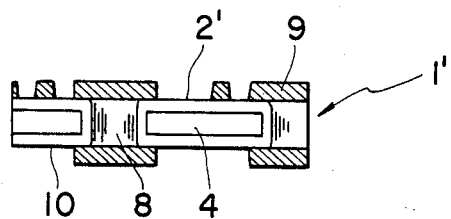
FIG. 17 is a sectional view taken on line XVII—XVII of FIG. 16.
Figure 18:
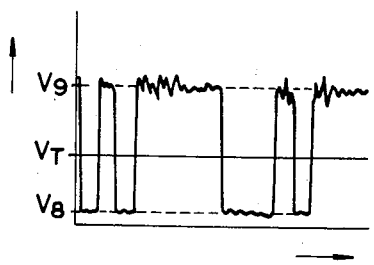
FIG. 18 is a graph showing a detection result obtained from the FIG. 16 semifinished product of printed circuit board.

Referring now to FIGS. 16 to 18, the manner of detecting the resist pattern with the apparatus of the embodiments set forth thus for will be described. The detection manner to be described herein may be carried out with the apparatus according to the previous embodiments of FIGS. 5, 9, 10, 12, 14 and 15.

FIG. 16 shows a wiring surface 2' of a semifinished product 1' of printed circuit board applied with a resist pattern 9. Exposed to portions other than the resist wiring pattern 9 is a copper foil 10. A sectional view taken on line XVII—XVII in FIG. 16 is illustrated in FIG. 17. This printed circuit board 1' formed with the copper foil 10 is applied with the resist pattern 9 which overlies the copper foil 10. FIG. 18 shows results of defect detection obtained by scanning the light ray along the XVII—XVII line of FIG. 16 using the pattern detecting apparatus according to the previous embodiments of this invention. In FIG. 18, the abscissa represents the position and the ordinate represents the voltage resulting from the photoelectric conversion by the detector. Voltage $V_8$ denotes a level corresponding to the copper foil 10, voltage $V_9$ a level corresponding to the resist wiring pattern 9, and voltage $V_T$ a threshold level. As evidenced by FIG. 18, the detection of the resist wiring pattern 9 can be achieved.

Figure 19:
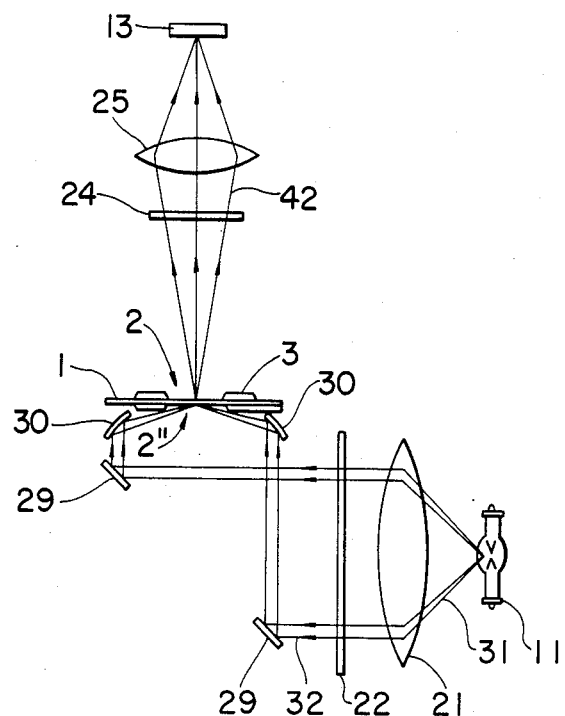
FIG. 19 is a side schematic showing a still further modified embodiment.
Figure 20:
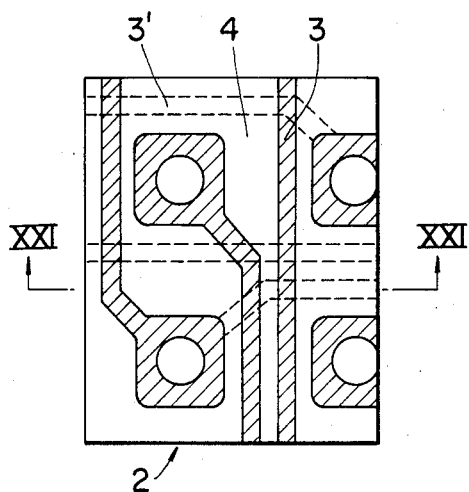
FIG. 20 is a plan view of another printed circuit board.

Turning to FIG. 19, a pattern detecting apparatus according to still further modification of the invention will be described. In FIG. 19, a printed circuit board 1, a filter 24, a focusing lens 25, and a detector 13 correspond to those of the FIG. 5 embodiment and are arranged in the same manner, but a high luminance light source 11" and a condensor lens 21" are disposed on the side of a wiring surface 2" which is in the rear of or opposite to the front wiring surface 2 of the printed circuit board 1 as shown in FIG. 20 and a light ray emitted from the high luminance light source 11" is obliquely incident from downward to the wiring surface 2". Thus, in comparison will the FIG. 5 embodiment, a pair of mirrors 29 and a pair of concave mirrors (or plane mirrors) 30 substitute for the half-mirror 23 of the embodiment in FIG. 5. Accordingly, a light ray 32" irradiating the wiring surface 2" transmits through the substrate 4 of the printed circuit board 1 as shown in FIG. 20 or passes through a through-hole and departs upwards from the wiring surface 2. The subsequent operation is substantially the same as that of the FIG. 5 embodiment but this embodiment of FIG. 19 has the following advantages.

Figure 21:
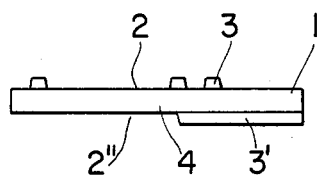
FIG. 21 is a sectional view taken on line XXI—XXI of FIG. 20.

In the embodiment of FIG. 5, if the filter 22 has such an incomplete optical filtering characteristic that a small quantity of light ray of more than 500 nm wavelength leaks through the filter 22, this leaking light ray will disadvantageously come into the detector 13, causing unwanted noises. However, in the embodiment of FIG. 19, there occurs no refected light ray from the surface (upper surface in the drawing) of the wiring pattern 3 and therefore, even with the filter 22" having an incomplete optical filtering characteristic, a leaking light ray cannot behave as a reflection light which would constitute a noise reaching the detector 13. Numeral 3' in FIGS. 20 and 21 denotes a wiring pattern on the back surface of the substrate 4. In addition, with a view of preventing the wiring pattern on the wiring surface 2" from shadowing the light ray incident to the substrate 4, the wiring surface is irradiated with the obliquely incident light ray in the FIG. 19 embodiment.

Figure 22:
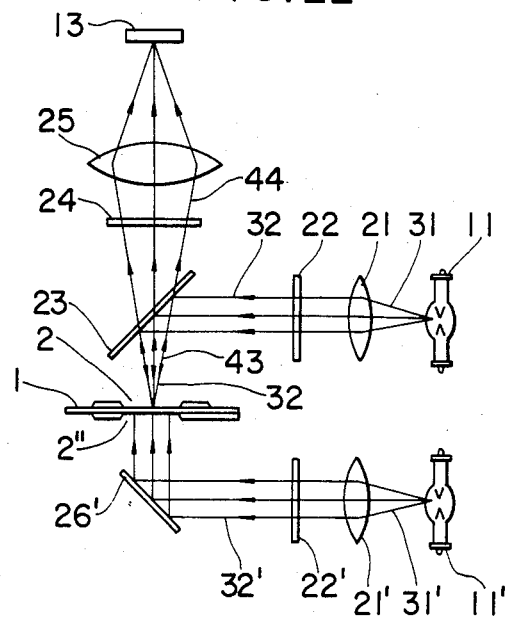
FIG. 22 is a side schematic showing a pattern detecting apparatus according to another embodiment of the invention.

FIG. 22 shows another embodiment of the present invention.

Figure 23:
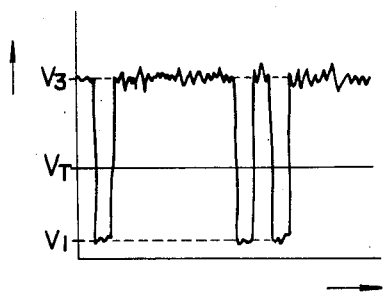
FIG. 23 is a graph showing a detection result along the line XXI—XXI of FIG. 20 obtained with the apparatus of the FIG. 22 embodiment.

In FIG. 22, a printed circuit board 1, a high luminance light source 11, a condensor lens 21, a filter 22, a half-mirror 23, a filter 24, a focusing lens 25 and a detector 13 are identical to those of the pattern detecting apparatus shown in FIG. 5 but a second high luminance light source 11', a second condensor lens 21', a second filter 22' and a mirror 26' are newly added. In FIG. 22, light rays 31 emitted from the light source 11 pass through the condensor lens 21 and come into the filter 22. Light rays 31' emitted from the second light source 11', on the other hand, pass through the condensor lens 21' and come into the filter 22'. The filters 22 and 21' are adapted to select among the light rays 31 and 31' respectively emitted from the light sources 11 and 11' only a light ray of a wavelength which can facilitate generation of a fluorescent radiation from the substrate of the printed circuit board 1. For example, these filters are of a so-called blue filter which transmits only a light ray of a wavelength ranging from 300 to 460 nm. The light ray passing through the filter 22, designated at 32, is changed by the half-mirror 23 in its path through 90° so as to be irradiated on a front wiring surface 2 of the printed circuit board 1. On the other hand, the light ray passing through the filter 22', designated at 32', is changed by the mirror 26' in its path through 90° so as to be irradiated on the wiring surface 2' in the rear of the wiring surface 2 of the printed circuit board 1. These light rays act as exciting light rays for generating fluorescent radiations from the substrate 4. The fluorescent radiations generated from the substrate 4 are mixed with a reflected light ray from the wiring surface 2, a transmission light ray transmitting through the substrate 4 and a light ray passing through the through-hole 8 to produce light rays 43 which come into the filter 24 after passing through the half-mirror 23. The filter 24 is adapted to separate the fluorescent radiation generated from the substrate 4 of the printed circuit board 1 from the other reflection light ray, transmission ray and passing light ray, and transmits only the fluorescent radiation designated at 44 having a wavelength different from that of the exciting light ray 32. For example, this filter 24 is a so-called yellow filter which reflects a light ray of a wavelength of less than 500 nm and transmits a light ray of a wavelength of more than 500 nm. The fluorescent radiation 44, separated from the reflected light ray from the wiring surface 2, the transmission light resulting from the light ray 32 incident to the wiring surface 2" and transmitting through the substrate 4 and the light ray passing through the through-hole 8 by means of the filter 24, is focused by the focusing lens 25 on a photoelectric conversion surface of the detector 13, thereby producing a negative image of a wiring pattern on the printed circuit board 1. Thus, according to the FIG. 22 embodiment of the present invention, the substrate 4 of the printed circuit board is excited by both the light ray 32 incident to the front wiring surface 2 and light ray 32' incident to the wiring surface 2" in the rear of the wiring surface 2 and hence the quantity of the fluorescent radiation generated from the substrate is increased, thereby ensuring that the signal to noise ratio of the detection signal detected by the detector 13 can be improved. With reference to FIG. 23, a detection result obtained with the pattern detecting apparatus of FIG. 22 will be described by making a comparison with the FIG. 8 embodiment. As in the case of the, FIG. 8 embodiment, the abscissa represent the position and the ordinate the voltage resulting from the photoelectric conversion by the detector 13 in a graphic representation shown in FIG. 23. The voltage $V_1$ indicative of the level corresponding to the wiring pattern 3 in FIG. 23 is equal to the level of the voltage $V_6$ of FIG. 8 embodiment whereas voltage $V_3$ indicative of the level corresponding to the substrate 4 in FIG. 23 is much higher than the voltage $V_7$ in the case of the FIG. 8 embodiment and the allowable set range of the voltage $V_T$ indicative of the threshold level is broader in FIG. 23 than in the FIG. 8 embodiment, indicating that the signal to noise ratio is improved.

Figure 24:
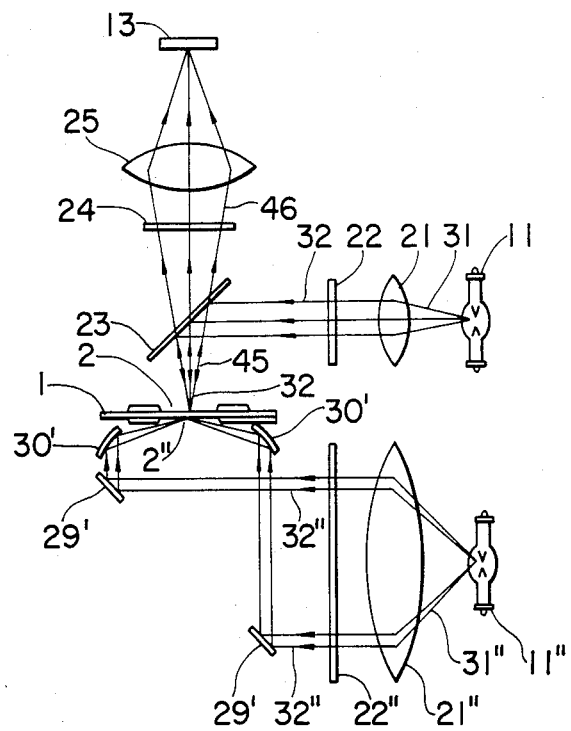
FIG. 24 is a side schematic showing a modification of the FIG. 22 embodiment, with which the FIG. 23 detection result is also obtained.

FIG. 24 shows a further modified embodiment wherein a printed circuit board 1, high luminance light sources 11 and 11", condensor lenses 21 and 21", filters 22 and 22", a half-mirror 23, a filter 24, a focusing lens 25, and a detector 13 correspond to those of the FIG. 22 embodiment and are arranged in the same manner but the mirror 26' of the FIG. 22 embodiment is replaced by mirrors 29' and concave or plane mirrors 30' in combination which are adapted to cause a light ray 32" to irradiate on a wiring surface 2" obliquely. The operation of this apparatus is the same as that of the FIG. 22 embodiment and will not be described herein. With a view of preventing the wiring pattern on the wiring surface 2" from shadowing the light ray incident to the substrate, the light ray 32" is obliquely irradiated on the wiring surface 2". In this embodiment, the detection signal indicative of the negative pattern image which is increased in amplitude and signal to noise ratio as in the FIG. 23 embodiment can be obtained.

Figure 25:
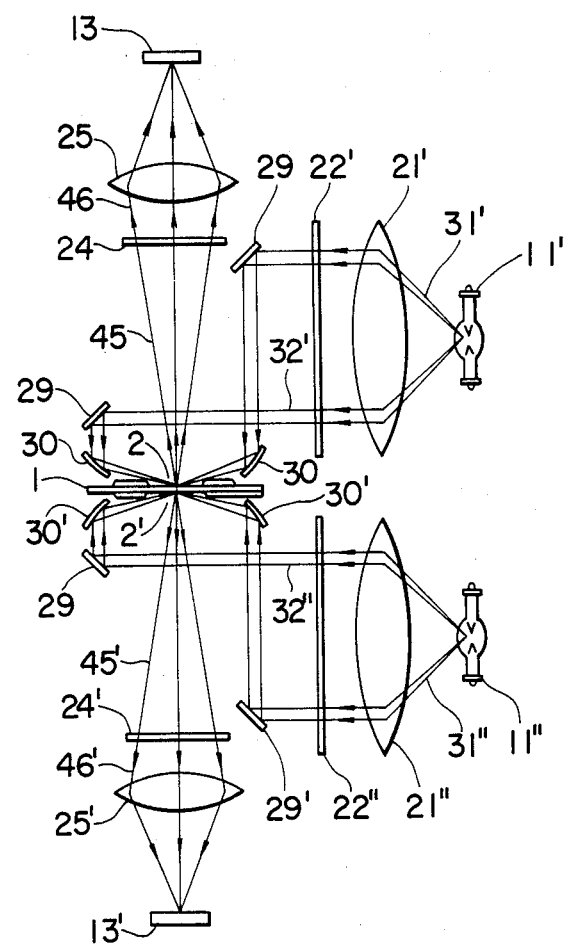
FIG. 25 is a side schematic showing another modification.
Figure 26A:
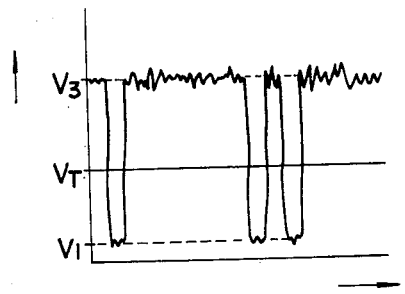
FIGS. 26A and 26B are graphical representations showing detection results along the line XXI—XXI of FIG. 20 obtained, with the apparatus of FIG. 25 modification, from a wiring front surface 2 and a rear wiring surface 2' opposite thereto, respectively.
Figure 26B:
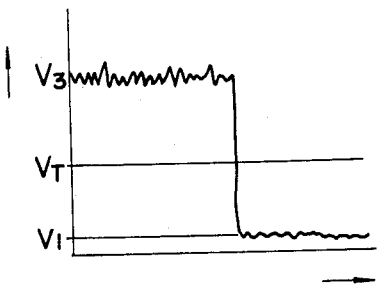

FIG. 25 shows still another modification wherein a printed circuit board 1, high luminance light sources 11' and 11", condensor lenses 21' and 21", filters 22' and 22", a mirror 29', a concave or plane mirror 30', a filter 24, a focusing lens 25 and a detector 13 correspond to those of the FIG. 24 embodiment and are arranged in the same manner. Being different from the FIG. 24 embodiment, this embodiment of FIG. 25 comprises mirrors 29 and concave or plane mirrors 30 in combination which substitute for the half-mirror 23 of the FIG. 24 embodiment, and additional filter 24', focusing lens 25' and detector 13'. The operation of the FIG. 25 embodiment is similar to that of the FIG. 22 embodiment in as much as the negative image of the wiring pattern on the wiring surface 2 of the printed circuit board 1 is focused on the photoelectric conversion surface of the detector 13 and will not be described herein. Especially, since, in this embodiment, the negative image of the wiring pattern on the wiring surface 2 can be detected by the detector 13 simultaneously with the detection of the negative image of the wiring pattern on the wiring surface 2' by means of the detector 13', the time required for the wiring pattern detection can be reduced considerably. Further, the substrate 4 of the printed circuit board 1 is excited by both the light ray 32' incident to the wiring surface 2 and light ray 32" incident to the wiring surface 2' in the rear of the wiring surface 2 and hence the quantity of the fluorescent radiation generated from the substrate is obviously increased as in the case of the FIG. 22 embodiment, thereby ensuring that the signal to noise ratio of the detection signals detected by the detectors 13 and 13' can be improved. FIGS. 26a and 26b show detection results along line XXI—XXI of FIG. 20 obtained, with the pattern detecting apparatus of FIG. 25 embodiment, from the wiring surface 2 and the wiring surface 2' opposite thereto, respectively. Needless to say, the detection result in FIG. 26a is identical to that in FIG. 23.

Although the present invention has been described by mainly referring to the exemplary case wherein the fluorescent radiation generated from the substrate of the printed circuit board is detected, teachings of the invention may of course be applicable effectively for a circuit pattern of a material excitable to emit a fluorescent radiation, for example, a resist pattern for etching purpose which is drawn on a substrate that is not excitable to emit a fluorescent radiation. Specifically, the present invention may be applied for inspection of a resist pattern for printed circuit board and a resist pattern for semiconductor circuit.

As has been described, according to the wiring pattern detecting apparatus of this invention, such an erroneous detection that the flaw and discoloration on the wiring pattern are detected as defect can be prevented, the adverse material such as copper residue can be detected as defect, and the presence or absence of defects even in the wiring pattern having the glossy wiring surface such a soldering pattern and a resist pattern can be detected correctly, thereby attaining highly significant, practical effects.

Specifically, with the simultaneous irradiation of light rays on both the front and rear wiring surfaces of the printed circuit board according to the present invention, the quantity of the fluorescent radiation generated from the substrate can be increased to improve the signal to noise ratio of the detection signal.

In addition, according to the invention, the wiring patterns on the front and rear wiring surfaces of the printed circuit board can be detected simultaneously by separate detectors to greatly reduce the time for the detection of the wiring patterns.

We claim:

1. An apparatus for detecting wiring patterns comprising:
    a source of light for emitting light rays to be irradiated on a wiring pattern formed on a wiring surface of an object to be detected;
    means for selecting among the light rays emitted from said light source light rays to be irradiated on the wiring pattern formed on the surface of said object in a direction substantially perpendicular to the surface of said object and having a wavelength having great ability to generate a fluorescent radiation in a direction perpendicular to said object;
    means for separating the fluorescent radiation emitted in the perpendicular direction from said object from reflected light rays from said object;
    a detector for detecting the fluorescent radiation; and
    optical means for focusing the fluorescent radiation generated from said object on said detector,
    wherein an image of the fluorescent radiation generated from portions on said wiring surface of said object excepting said wiring pattern is detected to obtain a negative pattern of said wiring pattern.

2. A pattern detecting apparatus according to claim 1 wherein said light source is a high luminance light source including one of a superhigh pressure mercury-arc lamp, a xenon lamp and a laser, and said fluorescent radiation detector is a high sensitivity linear array sensor.

3. A wiring pattern detecting apparatus according to claim 1 wherein said fluorescent radiation detector is a television camera, and means is provided for carrying and feeding stepwise said object, wherein a negative pattern of a wiring pattern on said wiring surface of said object is detected as still picture.

4. A wiring pattern detecting apparatus according to claim 4 wherein said light source is a stroboscope with means for lighting up the stroboscope in synchronism with a feed rate of said object, wherein a still picture is detected during continuous feed of said object.

5. A wiring pattern detecting apparatus according to claim 4 wherein shutter means is inserted in an optical path between said light source and fluorescent radiation detector, said shutter means being opened or closed in synchronism with a feed rate of said object, wherein a still picture is detected during continuous feed of said object.

6. A wiring pattern detecting apparatus according to claim 1 wherein said means for selecting the light ray for generating the fluorescent radiation and said means for separating the fluorescent radiation are constituted by a dichroic mirror.

7. A wiring pattern detecting apparatus according to claim 2 wherein said means for selecting the light ray for generating the fluorescent radiation and said means for separating the fluorescent radiation are constituted by a dichroic mirror.

8. A wiring pattern detecting apparatus according to claim 3 wherein said means for selecting the light ray for generating the fluorescent radiation and said means for separating the fluorescent radiation are constituted by a dichroic mirror.

9. A wiring pattern detecting apparatus according to claim 7 wherein said means for selecting the light ray for generating the fluorescent radiation and said means for separating the fluorescent radiation are constituted by a dichroic mirror.

10. A wiring pattern detecting apparatus according claim 7 wherein said means for selecting the light ray for generating the fluorescent radiation and said means for separating the fluorescent radiation are constituted by a dichroic mirror.

11. A wiring pattern detecting apparatus according to claim 4 wherein a mirror means is provided for irradiating the light rays emitted from said light source on the wiring surface of said object.

12. A wiring pattern detecting apparatus according to claim 4 wherein said light source is a laser light source and said fluorescent radiation detector is a photomultiplier, and wherein a scanning lens means is provided for focusing a laser beam into a spot beam, a rotary mirror means is provided for scanning the laser beam, and a set of optical fiber means are provided for guiding the fluorescent radiation generated from said object to said photomultiplier.

13. A wiring pattern detecting apparatus comprising:
    light means for emitting light rays having a wavelength with a large ability for exciting fluorescent light;
    mirror means positioned for reflecting the light rays from said light means so as to perpendicularly illuminate a printed circuit board having a wiring pattern and for passing therethrough fluorescent light emitted from said printed circuit board in response to the perpendicular light rays impinging thereon;
    a focusing lens positioned for focusing said fluorescent light passed through said mirror means so as to provide a fluorescent image; and photoelectric detector means including one of a television camera and a linear array sensor for converting the fluorescent image focused by said focusing lens into an image signal so as to enable formation of a negative pattern of the wiring pattern by detecting the image signal from said photoelectric detector means.

14. A wiring pattern detecting apparatus according to claim 13, wherein said mirror means reflects said light rays from said light means perpendicularly onto said printed circuit board so that fluorescent light is emitted from portions of said printed circuit board other than portions having the wiring pattern, said mirror means reflecting light rays having a wavelength less than a predetermined wavelength and passing therethrough fluorescent light having a wavelength greater than a predetermined wavelength.

15. A wiring pattern detecting apparatus according to claim 14, wherein said light means comprises a high luminance light source composed of a super high pressure mercury-arc lamp for emitting light rays therefrom toward said mirror means, a condenser lens for forming a beam of light rays onto said mirror means, and a filter disposed in the path of the beam of light rays between said condenser lens and as mirror means for selecting light rays of a predetermined wavelength range to impinge upon said mirror means.

16. A wiring pattern detecting apparatus according to claim 14, wherein said light means includes a high luminance light source composed of a laser beam source.

17. A wiring detecting apparatus according to claim 14, wherein said light means includes a stroboscope for emitting light rays therefrom toward said mirror means, a condenser lens for forming a beam of light ray onto said mirror means, and a filter disposed in the path of the beam of light rays between said condenser lens and said mirror means for selecting light rays of a predetermined wavelength range to impinge upon said mirror means.

18. A wiring pattern detecting apparatus according to claim 17, further comprising means for energizing the stroboscope in synchronism with a feed rate of said printed circuit board, wherein a still image is detected during continuous feed of said printed circuit board.

19. A wiring pattern detecting apparatus according to claim 14, wherein said photoelectric detecting means is a television camera, and further comprising means for carrying and feeding stepwise said printed circuit board, wherein a negative pattern of a wiring pattern on a wiring surface of said printed circuit board is detected as a still image.

20. A wiring pattern detecting apparatus according to claim 14, further comprising means for forming a negative pattern of the wiring pattern by detecting the image signal from said photoelectric detector means with a predetermined threshold level and converting the detected image signal to a binary signal.

21. A wiring pattern detecting apparatus according to claim 14, further comprising light means for illuminating a rear surface of said printed circuit board With light in an inclined direction with respect to the rear surface of said printed circuit board, said light having a wavelength with a large ability for exciting fluorescent light.

22. A wiring pattern detecting apparatus according to claim 14, wherein said mirror means includes a dichroic mirror.

23. A wiring pattern detecting apparatus according to claim 13, further comprising filter means positioned in a path between said mirror means and said photoelectric detector means for passing only fluorescent light therethrough to said photoelectric detector means.

24. A wiring pattern detecting apparatus according to claim 23, wherein said filter means is positioned in a path between said mirror means and said focusing lens for passing only fluorescent light therethrough to said focusing lens.

25. A method for detecting a wiring pattern on a printed circuit board comprising the steps of:
emitting light rays having a wavelength with a large ability for exciting fluorescent light from a light emitting means;
positioning a mirror means for reflecting the light rays from the light emitting means so as to perpendicularly illuminate a printed circuit board having a wiring pattern;
passing through the mirror means fluorescent light emitted from the printed circuit board in response to the perpendicular light rays impinging thereon;
positioning a focusing lens for focusing the fluorescent light passed through the mirror means so as to provide a fluorescent image; and
photoelectrically detecting and converting by one of a television camera and a linear array sensor the fluorescent image focused by the focusing lens into an image signal so as to enable formation of a negative pattern of the wiring pattern.

26. A method according to claim 25, wherein the mirror means is positioned to reflect the light rays from the light emitting means perpendicularly onto the printed circuit board so that fluorescent light is emitted from portions of the printed circuit board other than portions having the wiring pattern, and arranging the mirror means so as to reflect light rays having a wavelength less than a predetermined wavelength and to pass therethrough fluorescent light having a wavelength greater than a predetermined wavelength.

27. A method according to claim 26, wherein the step of emitting light rays includes providing a high luminance light source composed of a super high pressure mercury-arc lamp for emitting light rays therefrom toward the mirror means through a condenser lens for forming a beam of light rays onto the mirror means and through a filter disposed in the path of the beam of light rays between the condenser lens and the mirror means for selecting light rays of a predetermined wavelength range to impinge upon the mirror means.

28. A method according to claim 26, wherein the step of emitting light rays includes providing a high luminance light source composed of a laser beam source.

29. A method according to claim 26, wherein the step of emitting light rays includes providing a stroboscope for emitting light rays therefrom toward the mirror means through a condenser lens for forming a beam of light rays onto the mirror means, and through a filter disposed in the path of the beam of light rays between the condenser lens and the mirror means for selecting light rays of a predetermined wavelength range to impinge upon the mirror means.

30. A method according to claim 29, further comprising the step of energizing the stroboscope in synchronism with a feed rate of the printed circuit board, wherein a still image is detected during continuous feed of the printed circuit board.

31. A method according to claim 26, wherein the step of photoelectrically detecting includes utilizing a television camera, and further comprising the steps of carrying and feeding stepwise the printed circuit board, wherein a negative pattern of a wiring pattern on a wiring surface of the printed circuit board is detected as a still image.

32. A method according to claim 26, further comprising the step of forming a negative pattern by detecting the image signal with a predetermined threshold level and converting the detected image signal to a binary signal.

33. A method according to claim 26, further comprising the step of providing light means for illuminating a rear surface of the printed circuit board with light in an inclined direction with respect to the rear surface of the printed circuit board, the light having a wavelength with a large ability for exciting fluorescent light.

34. A method according to claim 26, further comprising the step of utilizing a dichroic mirror as the mirror means.

35. A method according to claim 25, further comprising the step of positioning a filter means in a path between the mirror means and the one of the television camera and the linear array sensor for passing only fluorescent light through the filter means to the one of the television camera and the linear array sensor.

36. A method according to claim 35, wherein the step of positioning the filter means includes positioning the filter means in a path between the mirror means and the focusing lens for passing only fluorescent light through the filter means to the focusing lens.

* * * * *

UNITED STATES PATENT AND TRADEMARK OFFICE
CERTIFICATE OF CORRECTION

PATENT NO. : 4,816,686
DATED : Mar. 28, 1989
INVENTOR(S) : Hara et al.

It is certified that error appears in the above-identified patent and that said Letters Patent is hereby corrected as shown below:

<u>Column 12</u>

Line 5, delete "claim 4" and insert --claim 1--

Line 10, delete "claim 4" and insert --claim 1--

Line 32, delete "claim 7" and insert --claim 4--

Line 37, delete "claim 7" and insert --claim 5--

Line 42, delete "claim 4" and insert --claim 1--

Line 46, delete "claim 4" and insert --claim 1--

Signed and Sealed this

Sixteenth Day of June, 1992

*Attest:*

DOUGLAS B. COMER

*Attesting Officer*  Acting Commissioner of Patents and Trademarks